United States Patent [19]

Hughes et al.

[11] Patent Number: 5,279,795
[45] Date of Patent: Jan. 18, 1994

[54] EXTENDED RANGE CHEMICAL SENSING APPARATUS

[75] Inventors: Robert C. Hughes; W. Kent Schubert, both of Albuquerque, N. Mex.

[73] Assignee: The United States of America as represented by the United States Department of Energy, Washington, D.C.

[21] Appl. No.: 171

[22] Filed: Jan. 4, 1993

[51] Int. Cl.⁵ ............................................. G01N 27/00
[52] U.S. Cl. ..................................... 422/98; 422/105; 73/23.2; 73/25.03; 73/31.06; 436/144; 436/149; 436/151
[58] Field of Search ............... 422/98, 105; 436/144, 436/151, 149; 73/25.03, 23.2, 31.06

[56] References Cited

U.S. PATENT DOCUMENTS

| | | | |
|---|---|---|---|
| 4,058,368 | 11/1977 | Svensson et al. | 23/254 |
| 4,313,907 | 2/1982 | McNally | 422/97 |
| 4,730,479 | 3/1988 | Pyke et al. | 73/23.21 |
| 4,885,929 | 12/1989 | Kasahara et al. | 422/98 |
| 4,892,834 | 1/1990 | Rauh | 436/149 |
| 4,916,935 | 4/1990 | Novack et al. | 422/98 |
| 4,931,851 | 6/1990 | Sibbald et al. | 357/25 |
| 4,953,387 | 9/1990 | Johnson et al. | 73/25.03 |
| 4,992,244 | 2/1991 | Grate | 422/98 |
| 5,045,285 | 9/1991 | Kolesar, Jr. | 422/98 |
| 5,071,770 | 12/1991 | Kolesar, Jr. | 422/98 |
| 5,143,696 | 9/1992 | Haas et al. | 422/90 |

FOREIGN PATENT DOCUMENTS 2239094  6/1991  United Kingdom .

OTHER PUBLICATIONS

"Thin Films of Pd/Ni Alloys for Detection of High Hydrogen Concentrations", J. Appl. Physics 71(1), Jan. 1, 1992, pp. 542-544.

Primary Examiner—James C. Housel
Assistant Examiner—Nina Bhat
Attorney, Agent, or Firm—Timothy D. Stanley

[57] ABSTRACT

An apparatus for sensing chemicals over extended range of concentrations. In particular, first and second sensors each having separate, but overlapping ranges for sensing concentrations of hydrogen are provided. Preferably, the first sensor is a MOS solid state device wherein the metal electrode or gate is a nickel alloy. The second sensor is a chemiresistor comprising a nickel alloy.

22 Claims, 5 Drawing Sheets

EXTENDED RANGE CHEMICAL SENSING APPARATUS

The United States Government has rights in this invention pursuant to Contract No. DE-AC04-76DP00789 between the Department of Energy and American Telephone and Telegraph Company.

BACKGROUND OF THE INVENTION

The present invention relates generally to chemical sensing apparatus and, more particularly, to apparatus for sensing hydrogen over an extended range of concentrations.

Providing chemical sensing apparatus, and especially apparatus for sensing hydrogen, having the capability to detect chemicals over an extended range of concentrations continues to present a technological challenge in spite of recent advance in the field of chemical sensing apparatus. While a wide variety of solid state chemical sensors have been developed, such sensors have generally been limited to detecting low concentrations of hydrogen. Exemplary of such solid state sensors include: metal-insulator-semiconductor (MIS) or metal-oxide-semiconductor (MOS) capacitors and field effect transistors (FET) as well as palladium gated diodes. A first MISFET sensor is described by Svensson et.al. in U.S. Pat. No. 4,058,368 wherein the metal electrode or gate is preferably palladium; although, Svennson et al. suggest that less sensitive devices could also be made with a nickel or platinum metal electrode. Improvements on such MISFET sensor are described by Sibbald et. al. in U.S. Pat. No. 4,931,851, wherein the metal electrode or gate comprises, either platinum or palladium and $SiO_2$ mixed with or deposited on an exposed surface of the metal electrode. Whereas, Raul in U.S. Pat. No. 4,892,834, describes the use of sandwiched layers of metal oxides, pure catalytic metals, insulated oxides and semiconducting material in forming his solid state chemical sensor. More recently, Hughes et al. describe a palladium silver alloy diode for sensing hydrogen in "Thin-film palladium and silver alloys and layers for metal-insulator-semiconductor sensor" *J. App. Phys.* 63(1), 1987 pgs. 1074–1083. Alternatively, McNally in U.S. Pat. No. 4,313,907 describes a chemical sensor employing a wheatstone bridge wherein one of the resistive legs comprises a platinum wire coated with a mixture of palladium, palladium oxide and nickel oxide. While Johnson et. al. in U.S. Pat. No. 4,953,387 describes an alternative resistive semiconductor device.

In spite of such advances, there remains a need for chemical sensing apparatus capable of detecting a dynamic range of hydrogen concentrations over at least six orders of magnitude (i.e. $10^6$). Moreover, there remains a need for a chemical sensing apparatus which responds rapidly and reversibly to changes in concentrations at room temperatures while resisting the poisoning effects of materials such as $H_2S$.

SUMMARY OF THE INVENTION

The present invention relates generally to apparatus for sensing chemicals. In particular, a chemical sensing apparatus is described for sensing hydrogen over an extended range of concentrations of at least six orders of magnitude. The chemical sensing apparatus includes a first sensor for sensing a selected chemical over a first range of concentrations as well as a second sensor for sensing the selected chemical over a second range of concentrations; wherein, the first and second ranges overlap. In particular, the first sensor can include either a MOS transistor or MOS capacitor wherein the electrode or metal gate comprises an alloy adapted to resist formation of a hydride phase over an extended range of hydrogen partial pressures or concentrations. The second sensor can include a resistor formed from an alloy adapted to resist hydride phase formation over an extended range of hydrogen partial pressures or concentration. Most advantageously, such alloys comprise about 8–20% (atom %) nickel and can include alloys of palladium and at least one metal selected from the group including platinum, chromium, rhodium, copper, and nickel. Chemical sensing apparatus according to the present invention provide a dramatic improvement over existing chemical sensing apparatus. In particular, they develop reproducible, large signals, as well as respond rapidly and reversibly to changes in hydrogen concentration, and exhibit resistance to poisoning. Unexpectedly, such sensing apparatus can also distinguish between hydrogen and hydrogen containing materials, such as formic acid. These and other advantages of the present invention will be discussed more completely below. However, it will be understood that the detailed description and specific examples are illustrative of the present invention and that those skilled in the art will recognize that various changes and modifications in materials and apparatus will be apparent without departing from the spirit and scope of the present invention.

BRIEF DESCRIPTION OF THE DRAWINGS

The accompanying drawings, which are incorporated in and from part of the specifications, illustrate the present invention and, together with the description, serve to explain the invention.

DETAILED DESCRIPTION OF THE INVENTION

In order to better understand the present invention, the following introductory discussion is provided. The use of palladium gated MOS solid state devices as chemical sensors has been quite extensive since the discovery of their sensitivity to low concentrations of hydrogen gas. It is generally believed that such solid state sensors work because of the catalytic action of palladium and the selective diffusion of hydrogen in palladium. Unfortunately, the catalytic action of such solid state sensors can often times be inhibited or poisoned by materials such as $H_2S$.

In bulk palladium, attainment of equilibrium concentrations of absorbed hydrogen on the surface of the catalytic metal and dissolved hydrogen at the catalytic metal-oxide layer interface can take minutes to hours for low concentrations of hydrogen (at room temperatures) depending on the particular composition of the catalytic metal. Once equilibrium has been achieved, such sensors do not generally respond accurately to decreases in hydrogen concentration (i.e. not reversible). While thin films of palladium can respond more rapidly, even in thin film alloys presently employed in many solid state chemical sensors have their limitations. In particular, thin films of palladium can undergo a transformation to a hydride phase when exposed to hydrogen partial pressures as low as about 5 Torr at ambient temperature. The resulting hydride phase causes the palladium films to blister and delaminate. The present invention provides a novel chemical sensing apparatus for detecting chemicals over an extended range of concentrations and one which can respond rapidly and reversibly to changes in the concentrations of the chemical being sensed as well as have enhanced resistance to poisonings and hydride phase formation as will be described below.

Figure 1:
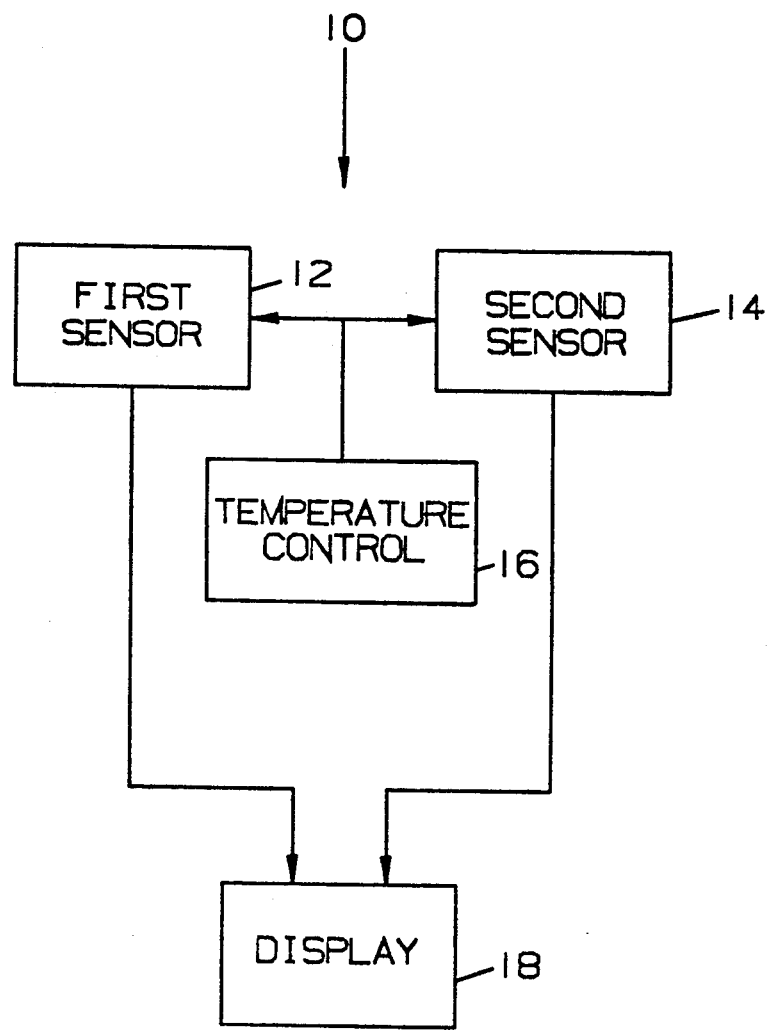
FIG. 1 comprises a block diagram of the present invention.

Looking now to FIG. 1, the present invention will initially be described. A chemical sensing apparatus 10 according to the present invention comprises a first sensor 12 for detecting a first range of concentrations of a chemical and a second sensor 14 for detecting a second range of concentrations of the chemical. The first and second concentration ranges overlap. The chemical sensing apparatus 10 can also include means 16 for compensating for variations in the operating temperature of the chemical sensing apparatus 10 as well as display means 18 for providing a measure of the concentration of the chemical sensed. The present invention is particularly useful in measuring changes in concentration of hydrogen and has also provided an unexpected ability to distinguish hydrogen ($H_2$) from hydrogen containing materials such as formic acid.

Figure 2:
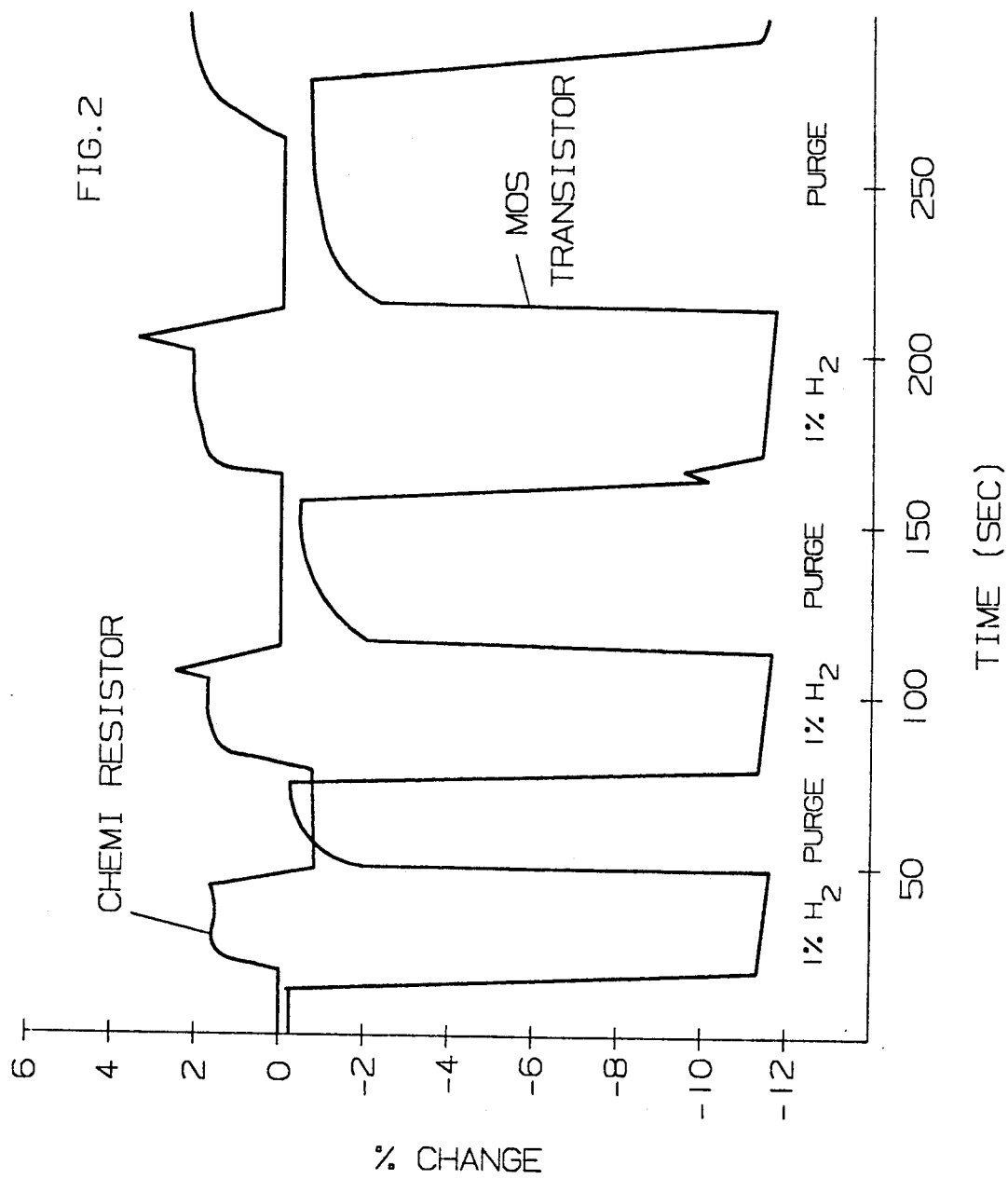
FIG. 2 depicts the response of a MOS transistor according to the present invention to changes in the concentration of hydrogen.
Figure 3:
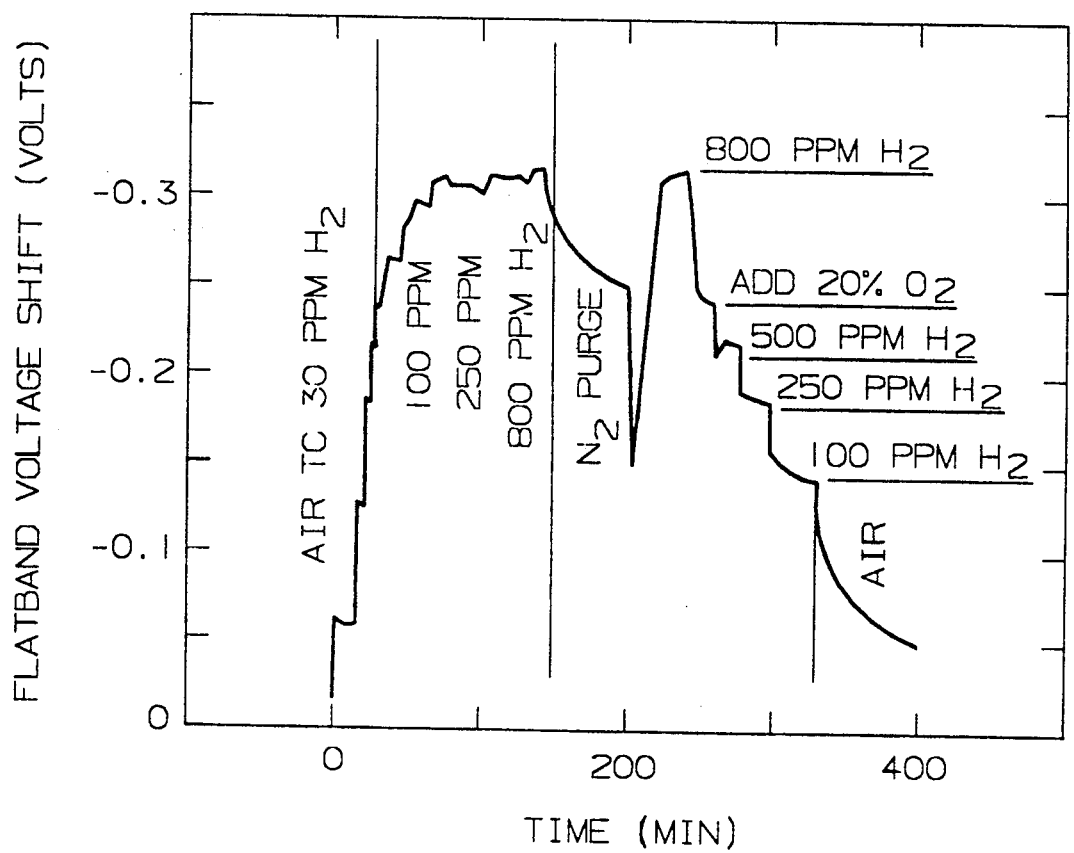
FIG. 3 depicts the response of a MOS capacitor according to the present invention to changes in the concentration of hydrogen.

The first sensor 12 comprises a gated metal-oxide-semiconductor (MOS) or metal-insulator-semiconductor (MIS) solid state device which respond rapidly and reversibly to changes in hydrogen concentration. In one embodiment, the MOS device preferably comprises a MOS transistor and can alternatively comprise a MOS capacitor. As depicted in FIGS. 2 and 3 respectively, MOS transistors and MOS capacitors, according to present invention, can respond rapidly and reversibly to changes in the concentration of hydrogen. In particular, FIG. 2 depicts the response time of a MOS transistor according to present invention to a cyclic exposure to gas containing 1% hydrogen followed by a purge of the hydrogen as well as the simultaneous response of a chemiresistor, which will be described below. FIG. 3 depicts the response time of a MOS capacitor according to the present invention to a variety of concentrations of hydrogen ranging from about 30 ppm to 800 ppm.

While MOS capacitors are simpler to fabricate than MOS transistors, MOS capacitors require measuring changes in capacitance to measure changes in the concentration of hydrogen. The measurement of capacitance requires measuring changes in AC signals which can be susceptible to electric noise and interference; whereas, MOS transistors require only the measurement of changes in DC voltage signals. Additionally, because of the smaller catalytic metal gate area of MOS transistors than MOS capacitors, the long term reliability of MOS transistors can be greatly enhanced. Typically, both such MOS devices can detect concentrations of hydrogen over a range of about 1 ppm to 1000 ppm. The lower detection limit of the MOS capacitor or MOS transistor is determined by the response time at lower concentrations. The limit of 1 ppm is a practical one since the time required for 90% of full scale signal is roughly proportional to the hydrogen pressure and can also depend on the operating temperature. The upper limit of 1000 ppm is the partial pressure at which the signal is almost saturated.

Figure 4:
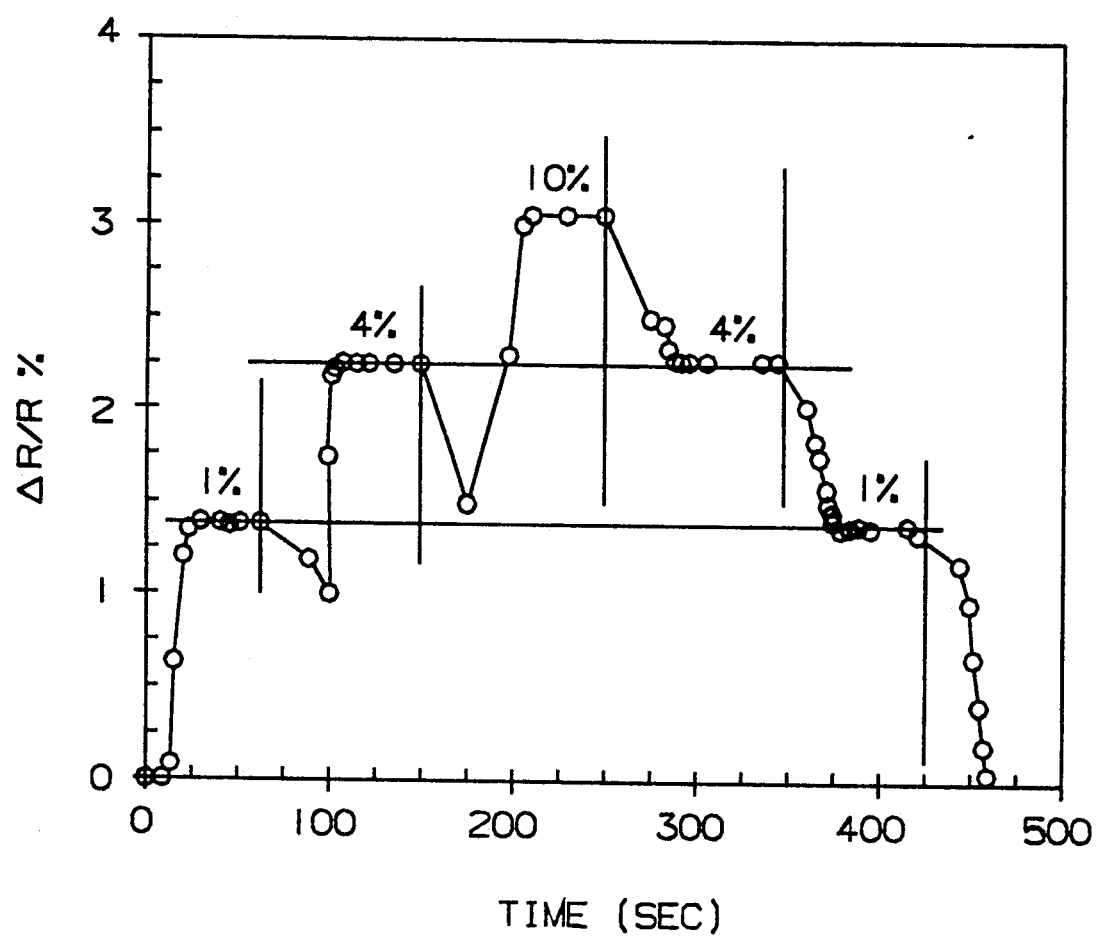
FIG. 4 depicts the response of a catalytic metal resistor according to the present invention to changes in the concentration of hydrogen.

The second sensor 14 comprises a catalytic metal resistor which is typically referred to as chemiresistor. As depicted in FIGS. 2 and 4, chemiresistors, according to the present invention, respond rapidly and reversibly to changes in the concentration of hydrogen. Typically, such chemiresistors can detect concentrations of hydrogen ranging from about 100 ppm to 100% (i.e., 1,000,000 ppm). As with the MOS solid state devices, the speed of response of the chemiresistor is proportional to the hydrogen partial pressure. The fastest response is at the highest partial pressure. At the lower partial pressures, the chemiresistor signal can be lost in noise.

An important aspect of the present invention is the composition of the metal alloy used as the metal electrode or gate in MOS solid state devices and in chemiresistors. Unlike typical sensing apparatus employing palladium, the alloys of the present invention effectively resist the formation of a hydride phase of the catalytic metal contained therein. Alloys of nickel and palladium have been most effective; however, alloys of nickel with other catalytic metals such as platinum, and rhodium, as well as alloys of palladium and copper, palladium and platinum and palladium and chromium are also believed to be effective. Alloys of about 8 to 20% (by atom %) nickel and the balance palladium have been found to be most effective. However, alloys containing greater than approximately 56% (by atom %) nickel and the balance palladium have been found insensitive to changes in hydrogen concentration.

To ensure a uniform alloy of nickel in the MOS solid state devices and chemiresistors, thin films (500 to 2000 Å) of such alloys can be deposited using a dual electron beam evaporator with dual thickness monitors to give accurate, complete mixing of the alloys. It is believed that sputtering techniques can also produce similar results. Composition of the deposited nickel alloys can be verified by Auger electron spectroscopy.

As with almost all metal films, the chemiresistor has a temperature coefficient of resistance (TCR) that is linear. The TCR is large enough that a temperature correction to the signal must be made. As such, temperature control means 16 are provided for maintaining the temperature of operation of the sensing apparatus 10 and can include a feed back circuit having a resistor insensitive to changes in the concentration of hydrogen to act as a heat source to maintain a selected operating temperature as well as a resistor to act as a temperature sensor. As depicted in FIG. 1, the temperature control means 16 operates to maintain a fixed temperature for both sensors. For example, a chemiresistor of composition of at least 56% nickel and the balance palladium could be adapted for both uses.

The sensing apparatus 10 can also include display means 18 by providing a measure of the hydrogen concentration sensed. By way of example, such display means 18 can include a computer for processing the signals developed by the first and second sensors as well as a display device.

Fabrication of the sensing apparatus 10 can be achieved by shadow masking or photolithography deposition technologies. In particular, both MOS solid state devices and chemiresistors can be fabricated on a single chip. Additionally, placement of temperature control means 15 for maintaining the operating temperature of the apparatus 10 can similarly be fabricated.

EXAMPLE

Figure 5:
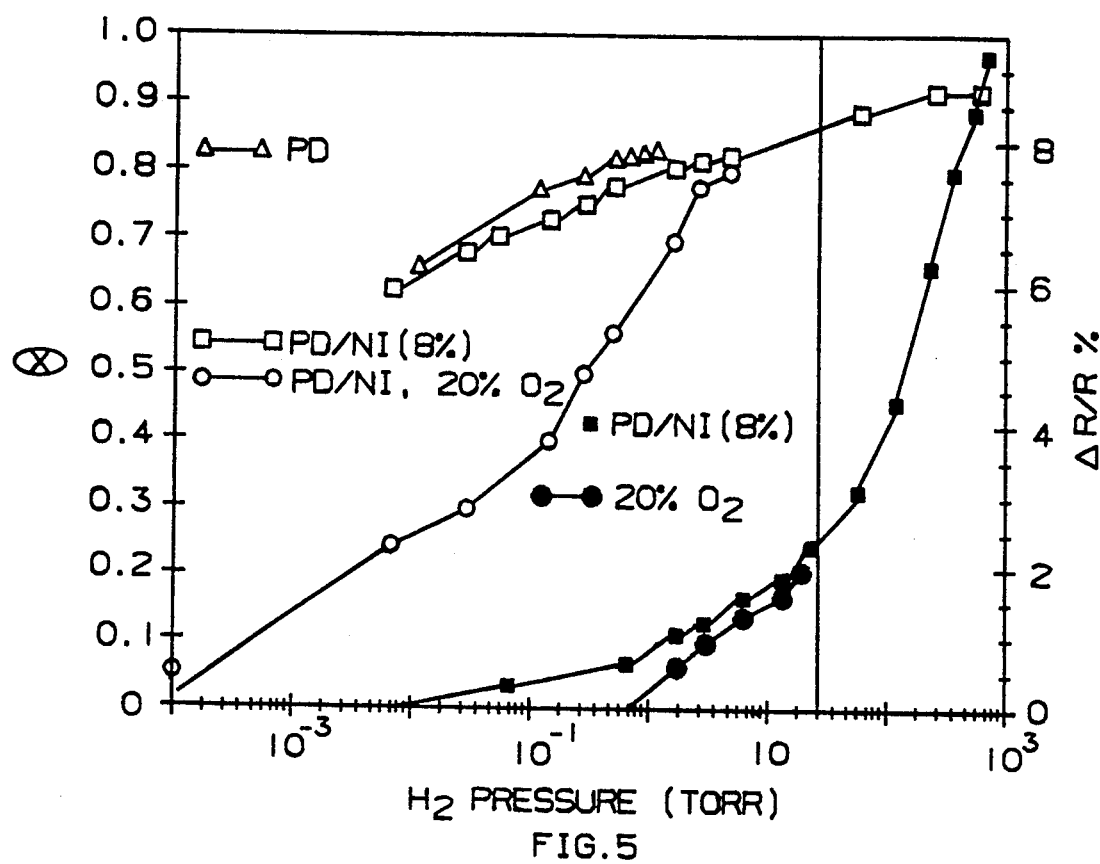
FIG. 5 compares the response of chemical sensors according to the present invention.

The construction and testing of a chemical sensing apparatus according to present invention will now be described. A 500 Å film, having a composition of about 8% Ni, and 92% Pd, was evaporated onto a flat substrate of $SiO_2$ deposited on a silicon wafer. In this example, the Si with $SiO_2$ wafer is a convenient flat, insulating, durable substrate to form a chemiresistor. A MOS capacitor was formed using a similar deposition technique. The responses were measured at 22° C. over seven decades of partial pressures of hydrogen as depicted in FIG. 5, The solid boxes depict the response of the chemiresistor, with changes in resistance shown on the right hand scale. The solid dots show the effect of a mixture of 20% partial pressure of oxygen on the signals from the chemiresistor. The open boxes depict the response of the MOS capacitor, with changes in surface covered on the left scale, which is proportional to changes in flat band voltage shift. The open circles depict the effect of a mixture of 20% partial pressure of oxygen on the signals from the MOS capacitor. The open triangles refer to a MOS capacitor having a pure palladium gate. The vertical line represents a demarcation between explosive and non explosive mixtures of hydrogen when an oxidant is present. The critical difference between the signal at 1% and 4% concentration of hydrogen can easily be seen. (i.e. non-explosive vs. explosive mixtures). The response of the MOS device depicted in FIG. 5 is the same alloy as the chemiresistor, but it responds to $H_2$ by a fundamentally different mechanism and responds to much smaller concentrations of $H_2$ (down to 1 ppm $H_2$) than the chemiresistor (generally no less than 100 ppm $H_2$).

Figure 6:
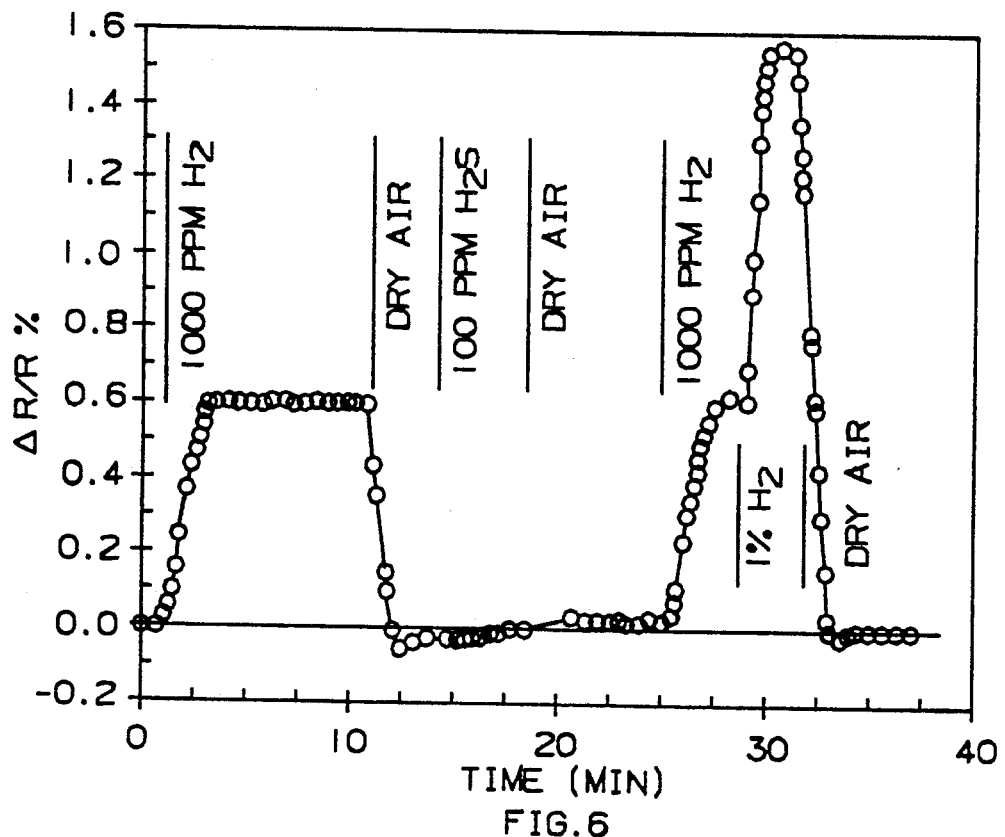
FIG. 6 depicts the response of a chemiresistor according to the present invention before and after exposure to $H_2S$.

Palladium and its alloys are notorious for losing their activity due to surface poisoning, and $H_2S$ is one of the worst poisons. A chemiresistor, according to the present invention, was exposed to about 100 ppm of $H_2S$ at 22° C. for 5 min. and showed little effect of poisoning as depicted in FIG. 6. Earlier tests on diodes with pure Pd gates showed a factor of 100 slowing of response after exposures to the same amount of $H_2S$. Additionally, chemical sensing apparatus according to the present invention have also shown a surprising and unexpected ability to distinguish hydrogen from hydrogen containing materials such as formic acid.

While particular embodiments of the present invention have been described for chemical sensing apparatus, it is not intended that the invention be limited thereby. Moreover, it will be apparent to those skilled in the art that various changes and modifications may be made to the invention as described without departing from the scope of claims appended hereto.

We claim:

1. An apparatus for sensing chemicals over an extended range of concentrations comprising:
    a. semiconductor sensor means for sensing a first range of concentrations of a chemical; and
    b. resistive sensor means for sensing a second range of concentrations of the chemical, wherein the first and second ranges of concentrations overlap.

2. The apparatus of claim 1, wherein said semiconductor sensor means comprises a metal-oxide semiconductor (MOS) solid state device.

3. The apparatus of claim 2, wherein the MOS device comprises a MOS transistor.

4. The apparatus of claim 2, wherein the MOS device comprises a MOS capacitor.

5. The apparatus of claim 2, wherein the metal gate or electrode of the MOS device comprises a nickel containing alloy adapted to resist formation of a hydride phase of the alloy.

6. The apparatus of claim 5, wherein the metal gate comprises an alloy of palladium and at least 8% nickel.

7. The apparatus of claim 5, wherein the metal gate comprises an alloy of palladium and no more than 20% nickel.

8. The apparatus of claim 5, wherein the nickel containing alloy includes at least one of the metals selected from the group consisting of platinum, rhodium, palladium, and combinations thereof.

9. The apparatus of claim 5 wherein the metal comprises an alloy of palladium and at least one metal selected from the group consisting of nickel, platinum, chromium, copper, rhodium, and combinations thereof.

10. The apparatus of claim 9, further including means for distinguishing hydrogen from hydrogen containing materials.

11. The apparatus of claim 1, wherein said resistive sensor means comprises a catalytic metal resistor.

12. The apparatus of claim 11, wherein the catalytic metal resistor comprises a nickel containing alloy adapted to resist formation of a hydride phase of the alloy.

13. The apparatus of claim 12, wherein the catalytic metal resistor comprises an alloy of palladium and at least 8% nickel.

14. The apparatus of claim 12, wherein the catalytic metal resistor comprises an alloy of palladium and no more than 20% nickel.

15. The apparatus of claim 1, wherein the first and second ranges of concentrations have a combined range of substantially 1 ppm to 1,000,000 ppm.

16. The apparatus of claim 1, further including third means for compensating for variations in the temperature of operation of the apparatus.

17. The apparatus of claim 1 wherein said semiconductor sensor has a rapid and reversible response to dynamic ranges of chemical concentrations at room temperature while resisting the harmful effects of certain chemicals.

18. The apparatus of claim 1 wherein said resistive sensor has a rapid and reversible response to dynamic ranges of chemical concentrations at room temperature while resisting the harmful effects of certain chemicals.

19. An apparatus for sensing hydrogen over an extended range of concentrations comprising:
    a. a metal-insulator-semiconductor (MIS) device adapted to sense a first range of hydrogen concentrations; and
    b. a chemiresistor adapted to sense a second range of hydrogen concentrations, wherein the first and second range of concentrations overlap.

20. The apparatus of claim 19, wherein the MIS device includes a metal electrode or gate comprises an alloy of about 8-20% nickel.

21. The apparatus of claim 19, wherein the chemiresistor comprises an alloy of about 8-20% nickel.

22. The apparatus of claim 19, wherein the combined first and second ranges for measuring concentrations of hydrogen is at least six orders of magnitude.

* * * * *